(12) United States Patent
Kloke et al.

(10) Patent No.: US 12,059,387 B2
(45) Date of Patent: Aug. 13, 2024

(54) CHARGE DEVICES HAVING POSITIONING DEVICES AND PROCESSES FOR CLOSING RECEPTACLES WITH VENTING

(71) Applicant: SCHOTT PHARMA SCHWEIZ AG, St. Gallen (CH)

(72) Inventors: Arne Kloke, St. Gallen (CH); Anil-Kumar Busimi, St. Gallen (CH); Dominique Bauert, St. Gallen (CH)

(73) Assignee: SCHOTT PHARMA SCHWEIZ AG, St. Gallen (CH)

( * ) Notice: Subject to any disclaimer, the term of this patent is extended or adjusted under 35 U.S.C. 154(b) by 791 days.

(21) Appl. No.: 17/017,752

(22) Filed: Sep. 11, 2020

(65) Prior Publication Data
US 2021/0069060 A1 Mar. 11, 2021

(30) Foreign Application Priority Data
Sep. 11, 2019 (EP) .................................... 19196826

(51) Int. Cl.
*B65D 69/00* (2006.01)
*A61J 1/16* (2023.01)
*A61L 2/26* (2006.01)
*A61J 1/05* (2006.01)

(52) U.S. Cl.
CPC .................. *A61J 1/16* (2013.01); *A61L 2/26* (2013.01); *A61J 1/05* (2013.01); *A61L 2202/18* (2013.01); *A61L 2202/24* (2013.01)

(58) Field of Classification Search
CPC ....... A61J 1/16; A61J 1/05; A61L 2/26; A61L 2202/18; A61L 2202/24; A61M 5/008; B65D 25/108; B65D 71/70; B65B 1/04; B65B 3/003

USPC ......... 206/363, 364, 370, 571, 438; 53/320, 53/321, 324, 489
See application file for complete search history.

(56) References Cited

U.S. PATENT DOCUMENTS

| | | | | |
|---|---|---|---|---|
| 4,286,389 A | * | 9/1981 | Ogle | ........................ B65B 3/003 215/307 |
| 5,519,984 A | | 5/1996 | Beussink | |
| 6,164,044 A | * | 12/2000 | Porfano | ................ A61M 5/344 53/489 |
| 9,919,094 B2 | * | 3/2018 | Shimazaki | ............ A61M 5/284 |
| 2001/0052476 A1 | | 12/2001 | Heinz | |
| 2007/0272648 A1 | * | 11/2007 | Hamamoto | ............ B65D 51/20 215/277 |

(Continued)

FOREIGN PATENT DOCUMENTS

| | | |
|---|---|---|
| DE | 202017103606 | 8/2018 |
| WO | 2016166769 | 10/2016 |

OTHER PUBLICATIONS

DIN ISO 7619-1, Rubber, vulcanized or thermoplastic—Determination of indentation hardness—Part 1: Durometer method (Shore hardness) (ISO 7619-1:2010) English translation of DIN ISO 7619-1:2012-02, Feb. 2012, 15 pages.

*Primary Examiner* — Luan K Bui
(74) *Attorney, Agent, or Firm* — Ruggiero McAllister & McMahon LLC

(57) ABSTRACT

A charge device is provided that includes a charge barrel having a charge. The charge barrel has an exit aperture and a flexible positioning device at the exit aperture. The charge is located inside the charge barrel. The charge barrel is adapted and arranged so that the charge is able to exit the charge barrel via the exit aperture.

20 Claims, 5 Drawing Sheets

(56) References Cited

U.S. PATENT DOCUMENTS

| | | | |
|---|---|---|---|
| 2009/0095647 A1* | 4/2009 | Togashi | A61M 5/008 206/438 |
| 2012/0248057 A1* | 10/2012 | Bogle | A61J 1/1412 53/489 |
| 2014/0027332 A1 | 1/2014 | Pawlowski | |
| 2017/0348476 A1* | 12/2017 | Thompson | B65D 71/70 |

* cited by examiner

CHARGE DEVICES HAVING POSITIONING DEVICES AND PROCESSES FOR CLOSING RECEPTACLES WITH VENTING

CROSS REFERENCE TO RELATED APPLICATIONS

This application claims benefit under 35 USC § 119 of European Application 19196826.2 filed on Sep. 11, 2019, the entire contents of which are incorporated herein by reference.

BACKGROUND

1. Field of the Invention

The invention relates in general to a charge device having a positioning device. The invention relates in particular to a device, to a kit, to a process for closing receptacles, a use of a venting device and a use of a positioning device.

2. Description of Related Art

Pharmaceutical material can be provided in a number of forms and contained in a variety of different containers. In the case of a liquid pharmaceutical material, some common examples are ampules, vials, cartridges and syringes. Sterilization of a pharmaceutical material is a paramount concern and this in turn depends heavily on an appropriate stoppering process. A number of attempts have been made to provide automated processes which offer both a sterile enclosed product and improved throughputs. Some of these attempts are based on so-called nests, which hold containers or stoppers in a regular array for ease of processing.

One example of an attempt employing nests is WO 2016 166769 A1, in which a nest containing closures is aligned over a nest containing cartridges in order to transfer the closures to the cartridges.

German utility patent DE 20 2017 103 606 U1 discloses the use of vents in the receptacles of a nest for improving the evacuation of gas from the receptacles when the nest is operated in a vacuum.

U.S. Pat. No. 5,519,984 discloses the use of a tube for temporary insertion into a syringe during stoppering.

There is still a need to provide improved processes and devices for stoppering of containers filled with pharmaceutical materials.

SUMMARY

Generally, the object of the present invention is to at least partially overcome one or more disadvantages in the state of the art, in particular in relation to the closing of receptacles.

It is an object of the present invention to provide a device for closing a receptacle, preferably a pharmaceutical receptacle, with an increased process throughput.

It is an object of the present invention to provide a device for closing a receptacle, preferably a pharmaceutical receptacle, via a more convenient process.

It is an object of the present invention to provide a device for closing a receptacle, preferably a pharmaceutical receptacle, via a reduced number of process steps.

It is an object of the present invention to provide a device for closing a receptacle, preferably a pharmaceutical receptacle, in a process having a reduced batch cycle period.

It is an object of the present invention to provide a device for closing a receptacle, preferably a pharmaceutical receptacle, with a reduced requirement for equipment, in particular without the need for vacuum apparatus.

It is an object of the present invention to provide a device for closing a receptacle, preferably a pharmaceutical receptacle, at atmospheric pressure.

It is an object of the present invention to provide a device for closing a receptacle, preferably a pharmaceutical receptacle, with an increased purity of receptacle contents.

It is an object of the present invention to provide a process for closing a receptacle, preferably a pharmaceutical receptacle, with an increased process throughput.

It is an object of the present invention to provide a process for closing a receptacle, preferably a pharmaceutical receptacle, which is more convenient.

It is an object of the present invention to provide a process for closing a receptacle, preferably a pharmaceutical receptacle, which has a reduced number of steps.

It is an object of the present invention to provide a process for closing a receptacle, preferably a pharmaceutical receptacle, which has a reduced batch cycle period.

It is an object of the present invention to provide a process for closing a receptacle, preferably a pharmaceutical receptacle, with a reduced requirement for equipment, in particular without the need for vacuum apparatus.

It is an object of the present invention to provide a process for closing a receptacle, preferably a pharmaceutical receptacle, which can be performed at atmospheric pressure.

It is an object of the present invention to provide a process for closing a receptacle, preferably a pharmaceutical receptacle, with an increased purity of receptacle contents.

The following embodiments are preferred embodiments of this disclosure.

A charge device comprising a set of one or more charge barrels, each charge barrel having a charge, wherein for each charge barrel: the charge barrel has an exit aperture and a flexible positioning device at the exit aperture; the charge is located inside the charge barrel; the charge barrel is adapted and arranged so that the charge is able to exit the charge barrel via the exit aperture.

One or more of the charge barrels each have a venting device which is adapted and arranged to allow gas to escape from the charge barrel as a charge exits the charge barrel through the exit aperture.

The charge device has, for one or more of the venting devices, the venting device is a hole. A preferred hole is a slot.

The charge device has, for one or more of the charge barrels, the venting device is in the positioning device or in the charge barrel, preferably in the positioning device. In one aspect of this embodiment, the venting device is one or more holes in the positioning device, preferably one or more slots in the positioning device.

One or more of the charge barrels can be a polymer.

One or more of the charge barrels can be selected from the group consisting of: polypropylene, polyethylene, polyamide, polyoxymethylene, polyvinylchloride, thermoplastic polyurethane, thermoplastic elastomer, liquid silicone rubber and polylactate.

The charge device, wherein, for one or more of the charge barrels, the length of the charge barrel is not more than 3 times a length of the charge, preferably not more than 1.5 times, more preferably not more than 1.2 times. In one aspect of this embodiment, the charge barrel is elongate having an elongate extension and the length of the charge is in the direction of the elongate extension of the charge barrel. In another aspect of this embodiment, the device is adapted and arranged for the charge to be able to move in the charge barrel in a direction of motion and the length of the charge is in the direction of motion.

The charge device wherein, for one or more of the charge barrels, the distance of the charge from the exit aperture is not more than 4 times the length of the charge, preferably not more than 2 times, more preferably not more than 1.5 times. In one aspect of this embodiment, the charge barrel is elongate having an elongate extension and the length of the charge is in the direction of the elongate extension of the charge barrel. In another aspect of this embodiment, the device is adapted and arranged for the charge to be able to move in the charge barrel in a direction of motion and the length of the charge is in the direction of motion.

The charge device wherein the charge device has 3 or more charge barrels, preferably 10 or more, more preferably 20 or more, more preferably 50 or more.

The charge device wherein the charge barrels are held in a fixed position relative to each other.

The charge device wherein the charge barrels are parallel to each other. Parallel in this context preferably means having axes oriented at an angle of not more than 20° to each other, preferably not more than 5°, more preferably not more than 3°.

The charge device wherein the charge barrels are arranged in a pattern.

The charge device wherein one or more of the charges is selected from the group consisting of: a plunger a stopper, a seal and a seal cap, preferably a plunger.

The charge device wherein, for one or more of the charge barrels, the inner diameter of the charge barrel at the exit aperture is less than the inner diameter of the charge barrel at a point inside the charge barrel.

The charge device wherein the closest distance between a first charge barrel and a second charge barrel is greater than one eighth of a radius of the first charge barrel, preferably greater than one quarter of a radius of the first charge barrel, more preferably greater than a half of a radius of the first charge barrel.

The charge device wherein the closest distance between a first charge barrel and a second charge barrel is in the range from 3 to 8 mm, preferably in the range from 4 to 7 mm, more preferably in the range from 5 to 6 mm.

The charge device wherein the closest distance between a first charge barrel and a second charge barrel is not more than 8 mm, preferably not more than 7 mm, more preferably not more than 6 mm.

The charge device wherein the closest distance between a first charge barrel and a second charge barrel is not less than 3 mm, preferably not less than 4 mm, more preferably not less than 5 mm.

The charge device wherein the charge device is located inside a sterile container. Preferred containers are tubs, boxes, pouches and bags, or a combination of two or more thereof.

The charge device wherein one or more of the charges comprises a material having a Young's modulus less than that of the charge barrel.

The charge device wherein one or more of the charges comprises a thermoplastic elastomer. The thermoplastic elastomer preferably comprises a butyl group or a halogen or both. Preferred halogens in this context are fluorine, chlorine and bromine.

A kit comprising a charge device according to any of the preceding embodiments and a receptacle device, the receptacle device comprising one or more receptacle barrels, each receptacle barrel having a receptacle located inside it; wherein each receptacle has an entry aperture; wherein each receptacle is suitable to receive a charge from a charge barrel through its entry aperture.

The kit wherein the positioning device of a first charge barrel is complementary to the entry aperture of a first receptacle.

The kit wherein one or more of the set of receptacles is selected from the group consisting of: a cartridge, a syringe, a syringe precursor and a vial.

The kit wherein one or more of the receptacle barrels comprises a polymer.

The kit wherein one or more of the receptacle barrels comprises one or more selected from the group consisting of: polypropylene, polyethylene, polyamide, polyoxymethylene, polyvinylchloride, thermoplastic polyurethane, thermoplastic elastomer, liquid silicone rubber and polylactate.

The kit wherein a first charge is a closure for a first receptacle.

The kit wherein the charge barrels correspond one to one with the receptacle barrels.

The kit wherein the charge barrels are arranged in a pattern and the receptacle barrels are arranged in a complementary pattern.

The kit wherein the charge barrels are held in a fixed position relative to each other.

The kit wherein the receptacle barrels are parallel to each other. Parallel is this context preferably means having axes oriented at an angle of not more than 20° to each other, preferably not more than 5°, more preferably not more than 3°.

The wherein the receptacle barrels are arranged in a pattern.

The kit wherein the receptacle device is located inside a sterile container. Preferred containers are tubs, boxes, pouches and bags, or a combination of two or more thereof.

A process for preparing one or more closed receptacles comprising the following process steps: Providing a kit; Expelling one or more charges from charge barrels via their exit apertures into corresponding receptacles via their entry apertures.

The process wherein the pressure inside one or more of the receptacles, preferably in all of the receptacles pressure is at least $10^4$ Pa, preferably at least $5\times10^4$ Pa, more preferably at least $9\times10^4$ Pa. In one aspect of this embodiment, the process is performed at atmospheric pressure. In one aspect of this embodiment, the process is performed above atmospheric pressure. In one aspect of this embodiment, the process is performed at around $10^5$ Pa. In one aspect of this embodiment, the process is performed at over $10^5$ Pa.

The process wherein the expulsion step is affected by a pressurized gas. The temperature of the gas during expulsion is preferably below 200° C.

The process wherein a material is introduced into one or more of the receptacles between the providing and expelling steps. The material is preferably a liquid. The material is preferably a medicament. The material preferably comprises an active pharmaceutical ingredient.

In an alternative embodiment, a material is introduced into one or more of the receptacles, generally at some point in the process. The material is preferably a liquid. The material is preferably a medicament. The material preferably comprises an active pharmaceutical ingredient.

A use of a barrel having a venting device in a process for stoppering at a pressure of at least $10^4$ Pa, preferably at least $5\times10^4$ Pa, preferably at least $9\times10^4$ Pa. In one aspect of this embodiment, the process is performed at atmospheric pressure. At one aspect of this embodiment, the process is performed above atmospheric pressure. In one aspect of this embodiment, the process is performed at around $10^5$ Pa. In one aspect of this embodiment, the process is performed at over $10^5$ Pa.

A use of a barrel having a venting device for producing a closed receptacle.

The use wherein the closed receptacle is a cartridge, a syringe, a syringe precursor or a vial.

The use wherein the closed receptacle contains a pharmaceutical active ingredient.

The term "parallel" throughout this disclosure preferably means at an angle of not more than 20° to, preferably not more than 5°, more preferably not more than 3°.

Atmospheric pressure is taken in this document to be 101,325 Pa.

This disclosure refers in various places to one or many, in connection with charges, charge barrels, receptacles, receptacle barrels, ejection device, positioning device and other parts of the device or kit. In each case, it is preferred for there to be at least 10, preferably at least 20, more preferably at least 50.

BRIEF DESCRIPTION OF THE DRAWINGS

The following figures serve to further explain this disclosure. The figures are exemplary and do not limit the scope of the invention.

DETAILED DESCRIPTION

Charge Device

Figure 1:
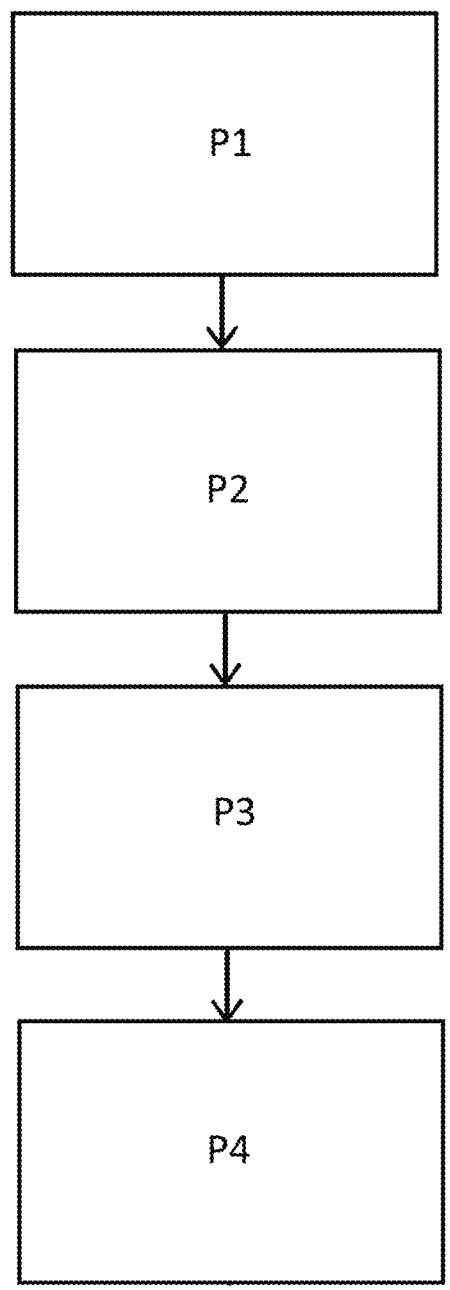
FIG. 1 shows a flow diagram for a process according to the invention.

A preferred charge device is adapted and arranged for applying a charge to a receptacle, preferably to close the receptacle.

The charge device according to the invention comprises one or more charge barrels, each charge barrel having a charge and a positioning device. Preferably, each charge barrel has a venting device.

The charge barrels are preferably in a fixed position relative to each other.

The charge device may comprise a charge support. A preferred charge support is adapted and arranged to hold the charge barrels in a fixed position relative to each other, preferably in a pattern. The charge barrels are preferably arranged in a pattern. The exit apertures of the charge barrels are preferably arranged in a pattern. A pattern can be a regular pattern or a nonregular pattern. A preferred pattern is a section of a regular lattice. Preferred regular lattices are hexagonal lattices and square lattices.

In one embodiment, the charge device comprises a charge support and the charge barrels and charge support are an integral member. In one aspect of this embodiment, the charge device and charge support are a molded plastic.

In one embodiment, the charge device comprises a charge support and the charge barrels and charge support are the same material, preferably are made of a same material.

The charge device preferably has a largest spatial extent in the range from 10 to 50 cm, preferably in the range from 20 to 40 cm.

Charge Barrels

The charge device according to the invention comprises a set of one or more charge barrels, the charge barrels each having an exit aperture. A preferred charge barrel is elongate.

A preferred charge barrel is hollow, preferably having an aperture at an end. In one embodiment, the charge barrel has an aperture at each of two ends. A preferred aperture is an exit aperture for a charge to exit the charge barrel. Another preferred aperture is adapted and arranged to allow an ejection device to act on a charge located in the charge barrel.

A preferred charge barrel is adapted and arranged for accommodating a charge. An accommodated charge is preferably held in the charge barrel, preferably held in the charge barrel by resilient contact with an interior surface of the charge barrel. A preferred charge barrel is adapted and arranged for ejecting a charge, preferably via the exit aperture. Ejection in this connection is preferably by an ejection device.

The charge barrels are preferably pre-loaded, each with a charge.

In a preferred embodiment, two or more of the set of charge barrels are parallel to each other, preferably all of the charge barrels are parallel to each other. A preferred arrangement of charge barrels is a battery of parallel charge barrels.

In a preferred embodiment, two or more of the set of charge barrels are adapted and arranged to eject charges in parallel directions, preferably all of the charge barrels are adapted and arranged to eject charges in parallel directions. Parallel in this context preferably means having axes oriented at an angle of not more than 20° to each other, preferably not more than 5°, more preferably not more than 3°.

A preferred charge barrel may comprise one or more retaining device for retaining a charge. Preferred retaining device are one or more selected from the group consisting of: a protrusion, a recess and a constriction. In one embodiment, the charge barrel has a retaining device for securing a charge from falling out the top end of the charge barrel. In one embodiment, the charge barrel has a retaining device for securing a charge from falling out the bottom end of the charge barrel. In one embodiment, the charge barrel has a retaining device for securing a charge from falling out the top end of the charge barrel and a retaining device for securing a charge from falling out the bottom end of the charge barrel.

In one embodiment, the charge barrel has one or more protrusions, preferably protruding from an inner surface of the charge barrel. Preferred protrusions are suitable for retaining a charge in the charge barrel. Preferably, a protrusion in the charge barrel complements a recess in a charge.

In one embodiment, the charge barrel has one or more recesses, preferably on an inner surface of the charge barrel. Preferred recesses are suitable for retaining a charge in the charge barrel.

Preferably, a recess in the charge barrel complements a protrusion in a charge.

In one embodiment, the positioning device is at an end of the charge barrel, wherein the inner diameter of the charge barrel at the end is less than an inner diameter of the charge barrel removed from the end.

The inner diameter of the charge barrel is preferably in the range from 5 to 20 mm, more preferably in the range from 8 to 15 mm, more preferably in the range from 9 to 12 mm.
Charge A preferred charge is adapted and arranged for closing a receptacle, preferably by resilient contact with an interior surface of the receptacle.

Preferred charges include an elastic material. An elastic material is preferably suitable for sealing a receptacle, preferably by resilient contact.

Preferred materials in this context are thermoplastic elastomers. Preferred thermoplastic elastomers comprise a butyl group.

Preferred thermoplastic elastomers comprise a halogen, preferably one or more selected from the group consisting of: fluorine, chlorine and bromine.

Preferred charges are stoppers and plungers.

In one embodiment, the charge is a plunger head, preferably for a syringe.

A charge may comprise one or more selected from the group consisting of: a protrusion and a recess. Preferred protrusions complement a recess in a charge barrel, preferably for retaining the charge in the charge barrel. Preferred recesses complement a protrusion in a charge barrel, preferably for retaining the charge in the charge barrel. Preferred protrusions are circumferential protrusions. Preferred recesses are circumferential recesses.

The diameter of the charge is preferably in the range from 5 to 20 mm, more preferably in the range from 8 to 15 mm, more preferably in the range from 9 to 12 mm.
Positioning Device Charge barrels according to the invention have positioning device. A positioning device is preferably adapted and arranged to position a charge barrel in relation to a receptacle barrel, preferably so that a charge exiting the charge barrel is able to enter the receptacle barrel, preferably to close a receptacle.

A positioning device and a charge barrel may be integrated, attached, fused or adhered with each other or a combination thereof.

In one embodiment, a charge barrel and a positioning device are made of the same material. In another embodiment, a charge barrel and a positioning device are made of different materials.

In one aspect of this embodiment, the positioning device has a lower Young's modulus than the charge barrel. In one aspect of this embodiment, the positioning device has a lower Shore hardness than the charge barrel.

In one embodiment, the charge has a lower Young's modulus than the positioning device. In one embodiment, the charge has a lower Shore hardness than the positioning device.

In one embodiment, the charge has a Shore-A hardness in the range from 30 to 80, preferably in the range from 35 to 70, more preferably in the range from 40 to 60.

In one embodiment, the positioning device has a Shore-A hardness of at least 30, preferably at least 60, more preferably at least 80. In one embodiment the positioning device has a Shore-D hardness of not more than 90, preferably not more than 80, more preferably not more than 70.

In one embodiment, the positioning device has a Shore-D hardness in the range from 20 to 90, preferably in the range from 30 to 80, more preferably from 40 to 70.

In one embodiment, the Shore hardness of the charge is less than that of the positioning device. Preferably, the Shore hardness of the charge is less than that of the positioning device by at least 1, more preferably by at least 10. It is preferred that the Shore-A hardness of the charge is less than that of the positioning device. Preferably, the Shore-A hardness of the charge is less than that of the positioning device by at least 1, more preferably by at least 10. It is preferred that the Shore-D hardness of the charge is less than that of the positioning device. Preferably, the Shore-D hardness of the charge is less than that of the positioning device by at least 1, more preferably by at least 10.

A preferred positioning device is a narrowing of a charge barrel. An inner diameter of the positioning device is preferably smaller than an inner diameter of the charge barrel. In one embodiment, an inner diameter of the positioning device is 1 to 4 mm smaller than an inner diameter of the charge barrel, preferably 1.25 to 3 mm, more preferably 1.5 to 2.5 mm.

A positioning device is preferably flexible.

A preferred positioning device is adapted and arranged to be introduced into a receptacle.

A preferred positioning device is adapted and arranged to be introduced into a receptacle barrel.

A preferred positioning device constitutes an extension of charge barrel.

In one embodiment, the positioning device is based on a hollow cylinder or a hollow prism, preferably a hollow cylinder. The positioning device may be an incomplete hollow prism or cylinder, preferably having one or more holes in a side wall. The positioning device preferably has an interior diameter which is smaller than an interior diameter of the charge barrel. The positioning device preferably has an interior dimeter which is smaller than an interior diameter of the receptacle. The positioning device preferably has an interior dimeter which is smaller than an interior diameter of the receptacle barrel. The positioning device preferably has an exterior diameter which is smaller than an interior diameter of the charge barrel. The positioning device preferably has an exterior dimeter which is smaller than an interior diameter of the receptacle. The positioning device preferably has an exterior dimeter which is smaller than an interior diameter of the receptacle barrel.

A preferred positioning device is a partial perimeter wall. A preferred perimeter wall constitutes between 30 and 70% of a full perimeter wall, preferably between 40 and 60%.

A preferred positioning device is a perimeter wall having one or more selected from the group consisting of: a hole, a slot and a gap.

A preferred position device consists of two or more sectional parts, preferably 2, 3, 4, 5 or 6, more preferably 3.

In one embodiment, one or more sectional parts has an axial slot having a circumferential extent of less than a third of the circumferential extent of the sectional part, preferably less than a quarter.

The positioning device may be tapered. Tapering may assist insertion of the positioning device into a receptacle or expulsion of a charge from the positioning device or both.

In one embodiment, the positioning device has a tapered section having its thickest end towards the charge barrel.

In one embodiment, the positioning device has a circumferential recess, preferably on its outer face. A circumferential recess is preferably in the superior half of the positioning device.

In one embodiment, the positioning device has a beveled lower end. The beveling is preferably on the outer face of the positioning device.

Venting Device

The device according to the invention comprises a venting device. A preferred venting device is adapted and arranged for allowing gas to escape from a charge barrel. A preferred venting device is adapted and arranged to allow the escape of gas pressured by a charge exiting a charge barrel.

A preferred venting device is a hole or a slot. A preferred hole or slot provides a passage between the interior of a charge barrel and outside the charge barrel. A preferred venting device is located in the charge barrel. Another preferred venting device is located in the positioning device.

Receptacle Device

A preferred receptacle device is adapted and arranged for receiving a charge in a receptacle, preferably to close the receptacle.

The receptacle device according to the invention comprises one or more receptacle barrels, each receptacle barrel having a receptacle.

The receptacle barrels are preferably in a fixed position relative to each other. The receptacles are preferably in a fixed position relative to each other.

The receptacle device may comprise a receptacle support. A preferred receptacle support is adapted and arranged to hold the receptacles in a position relative to each other.

In one embodiment, the receptacle device comprises a receptacle support and the receptacle barrels and receptacle support are an integral member. In one aspect of this embodiment, the receptacle device and receptacle support are a molded plastic.

In one embodiment, the receptacle device comprises a receptacle support and the receptacle barrels and receptacle support are the same material, preferably are made of a same material.

In one embodiment, the receptacles are slidably insertable into the receptacle barrels. In one embodiment, the receptacles are slidably removable from the receptacle barrels.

A receptacle device is disclosed in international patent document WO2016/166769 A1 in FIGS. 1 to 9 and the accompanying figure descriptions, which are incorporated by reference.

Receptacle Barrel

A receptacle device according to the invention comprises a set of one or more receptacle barrels, the receptacle barrels each having a receptacle inside.

A preferred receptacle barrel is elongate.

A preferred receptacle barrel is hollow, preferably having an aperture at an end, more preferably having an aperture at each of two ends. A preferred aperture is an entry aperture for a charge to enter the receptacle barrel.

A preferred receptacle barrel is adapted and arranged for accommodating a receptacle. An accommodated receptacle is preferably held in the receptacle barrel, preferably held in the receptacle barrel by abutting contact. In one embodiment, the receptacle abuts against a superior surface of the receptacle barrel. Abutment can be at the top of the receptacle or at the bottom of the receptacle. A preferred receptacle barrel is adapted and arranged for receiving a charge, preferably via an entry aperture. Receipt in this connection is preferably accompanied by closure of a receptacle, preferably closure of the entry aperture of the receptacle.

The receptacle barrels are preferably pre-loaded, each with a receptacle.

In a preferred embodiment, two or more of the set of receptacle barrels are parallel to each other, preferably all of the receptacle barrels are parallel to each other. A preferred arrangement of receptacle barrels is a battery of parallel receptacle barrels.

In a preferred embodiment, two or more of the set of receptacle barrels are adapted and arranged to eject charges in parallel directions, preferably all of the receptacle barrels are adapted and arranged to eject charges in parallel directions. Parallel is this context preferably means having axes oriented at an angle of not more than 20° to each other, preferably not more than 5°, more preferably not more than 3°.

In one embodiment, the receptacle barrel has a retaining device for holding the receptacle in a fixed position. Preferred retaining device are a lip, a protrusion, a recess and a flange. A preferred retaining device is adapted and arranged to complement a receptacle, preferably a lip, protrusion, recess or flange or a receptacle.

The inner diameter of the receptacle barrel is preferably in the range from 5 to 20 mm, more preferably in the range from 8 to 15 mm, more preferably in the range from 9 to 12 mm.

Receptacle

A preferred receptacle is adapted and arranged to contain a material, preferably a liquid, preferably a pharmaceutical product. Preferred receptacles are pharmaceutical receptacles.

A preferred receptacle is elongate. A preferred shape of the receptacle is a cylinder or a prism, preferably a cylinder.

A preferred receptacle has an interior. A preferred receptacle has one or more receptacle walls. A preferred receptacle has one or more receptacle apertures.

In one embodiment, a receptacle is elongate with an aperture at one end only. In another embodiment, a receptacle is elongate with an aperture at each of two ends.

Closure of a receptacle is preferably closure of a receptacle aperture. In one case, closure of a receptacle is closure of the sole receptacle aperture. In another case, closure of a receptacle is closure of one of two open receptacle apertures. In another case, closure of a receptacle is closure of the sole open receptacle aperture, the receptacle further having an already closed receptacle aperture.

A preferred receptacle corresponds with a charge. A preferred receptacle is suitable for receiving a charge. A preferred receptacle is suitable for being closed by a charge.

A preferred receptacle complements a receptacle barrel. A preferred receptacle is suitable for introducing into a receptacle barrel. A preferred receptacle is suitable for being removed from a receptacle barrel. A preferred receptacle has a cooperating part for positioning it in a receptacle barrel. A preferred cooperating part is a protrusion or a recess. One preferred protrusion is a flange. A preferred cooperating part in this context is suitable for abutment or resilient latching.

In one embodiment, the receptacle is a syringe precursor. A preferred syringe precursor has two apertures. A first aperture is the entry aperture for receiving the charge. The charge is preferably a plunger or a plunger head. A second aperture is an ejection aperture which is adapted and arranged to be attached to a needle. The second aperture is preferably closed during the process according to the invention.

A preferred receptacle is suitable for being retained by a receptacle barrel. A preferred receptacle can have a recess or a protrusion.

A receptacle is disclosed in international patent document WO2016/166769 A1 in FIGS. 6a and 6b and the accompanying figure descriptions, which are incorporated by reference.

Kit/Device

A charge device according to the invention and a receptacle device according to the invention are preferably employed in combination, preferably either as components of a device or as components of a kit, most preferably as components of a kit.

As a kit, the charge device and the receptacle device can be alignable or engageable with each other or both.

Sterile Enclosure

The charge device according to the invention or the kit according to the invention may be provided in a sterile enclosure. Sterile enclosures are disclosed in international patent document WO2016/166769 A1 in FIG. 9 and the accompanying figure descriptions, which are incorporated by reference.

Process

This disclosure provides a process for closing one or more receptacles. A preferred process is for closing 2 or more receptacles simultaneously, preferably 10 or more, more preferably 20 or more, more preferably 50 or more.

In the case of a kit according to this disclosure, the charges of the charge device are ejected from the charge barrels into the receptacles of the receptacle device. The charge device according to this invention can also be employed for closing receptacles not from a kit, but otherwise arranged in a position complementary to that of the charge barrels of the charge device.

The receptacles are preferably filled prior to being closed. The charge preferably closes the sole aperture of the receptacle or the sole remaining open aperture of the receptacle, one or more other apertures of the receptacle having been closed prior to filing.

In the process according to the invention, the charge preferably exits the positioning device at least partially. In one embodiment, the charge exits the positioning device only partially. It is preferred according to this embodiment for the charge to exit to an extent where the coefficient of friction between the charge and the inner face of the receptacle is greater than the coefficient of friction between the charge and the positioning device. In one embodiment, the charge exits the positioning device entirely. In one aspect of this embodiment, the charge moves to a position in which its top end is less than 4 mm below the bottom end of the positioning device, preferably less than 3 mm, more preferably less than 2 mm. In another aspect of this embodiment, the charge moves to a position in which its top end is more than 4 mm below the bottom end of the positioning device, preferably more than 5 mm, more preferably more than 6 mm. It is preferred for the charge to exit the positioning device entirely.

Ejection Device

A preferred ejection device is adapted and arranged for ejecting a charge from a charge barrel. A preferred ejection device maybe a located at an aperture of the charge barrel, preferably an aperture other than the exit aperture.

In one embodiment, the ejection device is adapted and arranged to eject the charge by virtue of a compressed gas. A compressed gas is at a pressure greater than the surrounding pressure. A preferred compressed gas is at a pressure of at least $2 \times 10^5$ Pa, preferably at least $3 \times 10^5$ Pa, most preferably at least $4 \times 10^5$ Pa. In another embodiment, the ejection device is adapted and arranged to eject the charge by mechanical pushing, for example a moveable pin.

Test Methods

Shore hardness. Shore-A and Shore-D are determined according to ISO 7619-1.

FIG. 1 shows a flow diagram for a process according to the invention. In a first step P1, a charge device 2 and a receptacle device 1 according to the invention are provided. This may consist in, for example, providing a kit containing a charge device 2 and a receptacle device 1.

In a second step P2, the receptacles 5 of the receptacle device 1 are filled, for example with a liquid comprising a pharmaceutical active ingredient. In a third step P3, the charge device 2 and receptacle device 1 are positioned relative to each other by introducing the positioning device 64 of the charge barrels 63 into the respective receptacles 5. In a fourth step P4, the charges 200 are ejected from the charge barrels 63 into the receptacles 5 to close them.

Figure 2A:
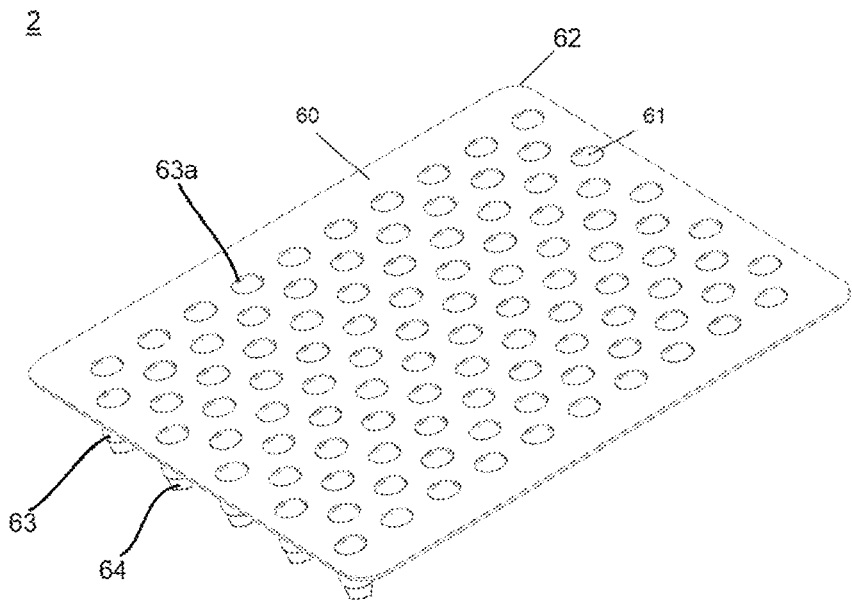
FIG. 2A shows a perspective view from above and to the side of a charge device.

FIG. 2A shows a perspective view from above and to the side of a charge device 2. The device 2 has 100 charge barrels 63, arranged in a hexagonal grid and held in position by a laminar charge support 60. In this case, the charge support 60 has a rectangular shape with curved corners 62. In this case, the charge barrels 63 and charge support 60 are an integral piece made of molded plastic. Each charge barrel 63 has an interior 61 which is adapted and adjusted for containing a charge 200 (charges not present in the figure). In this case, each charge barrel 63 has a protrusion 63A in its interior 61 which serves as a retaining device for a charge 200, retaining it by resisting upward movement. Each charge barrel 63 has a positioning device 64 at its lower end. In this case, the charge barrels 63 do not extend above the plane of the charge support 60, only below. In an alternative, the charge barrels 63 may extend above the plane of the charge support 60.

Figure 2B:
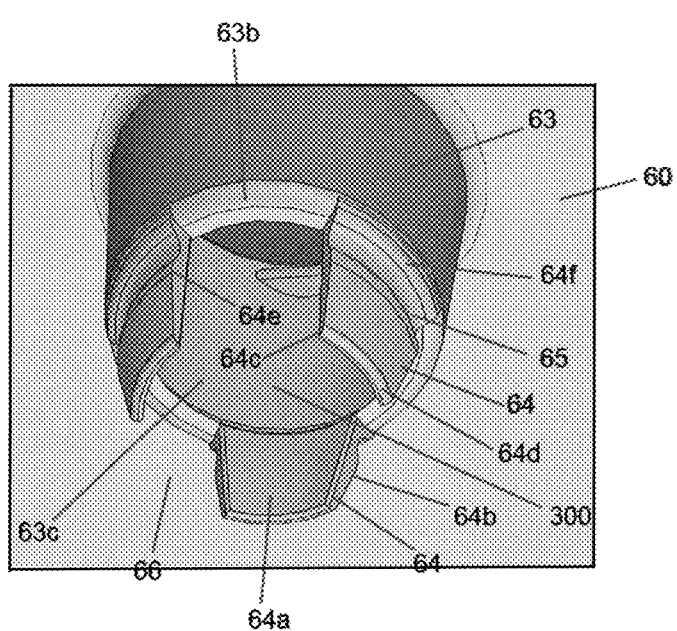
FIG. 2B shows a positioning device in perspective view from below.

FIG. 2B shows a positioning device 64 in perspective view from below and to the side. The positioning device 64 is located at the bottom rim 63B of a charge barrel 63, the charge barrel 63 being held in position by a charge support 60. In this case, the charge barrel 63 narrows towards its lower rim 63B such that the inner surface exhibits an inward taper 63C. The inward taper 63C, which constitutes a constriction of the charge barrel 63, may serve as a retaining device for the charge 200, retaining it by resisting downward movement of the charge 200. The positioning device 64 and the charge barrel 63 may together constitute a single integral part, or alternatively, the positioning device 64 may be attached or attachable to the charge barrel 63. The positioning device 64 in this case consists of 3 parts which form an extension of the side wall of the charge barrel 63. Together, the three extensions constitute roughly 50% of a perimeter wall. The gaps in between the 3 parts constitute 3 major gaps 66 in the positioning device 64, which function as a venting device for allowing gas to move from the interior of the positioning device 64 to outside. This venting allows evacuation of gas in front of a charge 200 (not in position in the figure) as it is ejected from the charge barrel 63. The positioning device 64 has a circumferential recess 65 immediately following its top end 64f, where it meets the charge barrel 63. The circumferential recess 65 facilitates air flow as well as flexion of the positioning device 64. Below the circumferential recess 65, the positioning device 64 has its thickest point 64e after which it tapers in towards its lower end 64c. At its lower end 64c, the outer surface of the positioning device 64 is beveled inwards 64d. The lower end 64c of the positioning device 64 is open and in this case constitutes a circular exit aperture 300. Both the tapering and the beveling facilitate location of the positioning device 64 inside a receptacle 5 (not shown). In this case, the inner surface 64A of the positioning device 64 has a cylindrical form and the variation in the thickness is manifest on the outer surface 64B.

Figure 2C:
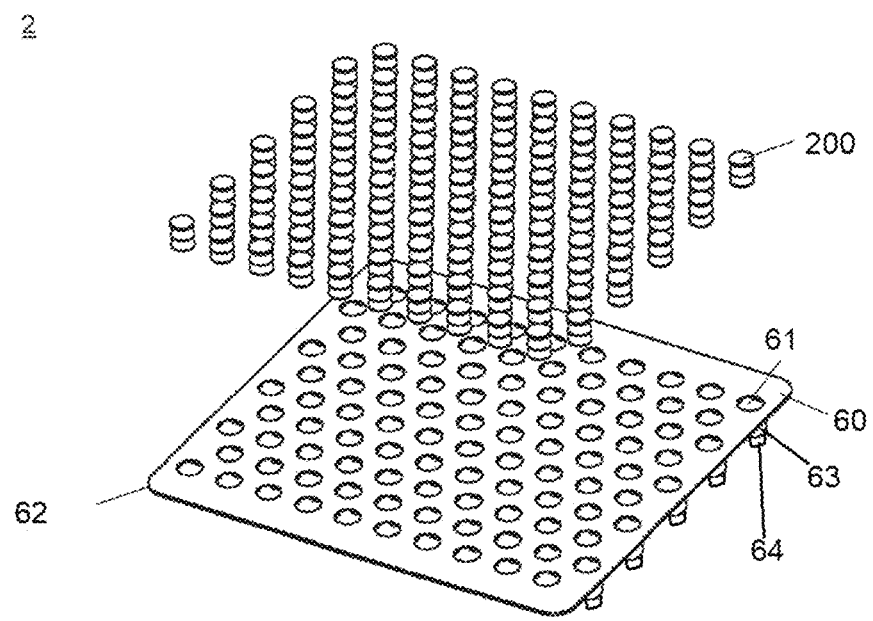
FIG. 2C shows the charging of a charge device in perspective view from above.

FIG. 2C shows the charging of a charge device 2 in perspective view from above. The charge device 2 has 100 charge barrels 63, held in a regular array by a charge support 60, in this case in a rectangular shape with rounded corners 62. 100 charges 200 are positioned above the array of 100 charge barrels 63, ready to be introduced into their interiors 61.

Figure 2D:
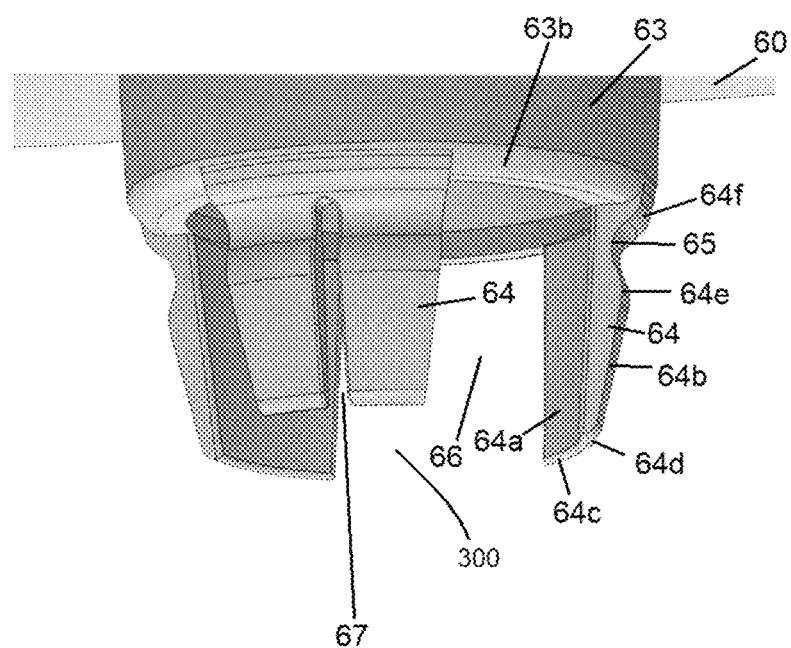
FIG. 2D shows a positioning device in perspective view from below.

FIG. 2D shows a positioning device 64 in perspective view from below. This positioning device 64, like that of FIG. 2B, has three parts which constitute extensions of the cylindrical walls of the charge barrel 63. Again, the charge barrel 63 is held in place by a charge support 60 and the positioning device 64 is attached to the bottom rim 63B of the charge barrel 63. The lower end 64c of the positioning device 64 is open and in this case constitutes a circular exit aperture 300. The positioning device 64 from top 64f to bottom 64c exhibits the circumferential recess 65 followed by an apex 64e, an inwardly tapered outer surface 64B and an inwardly beveled end 64d. The inner surface 64A of the positioning device again is tapered inwards so as to constrict towards its lower end 64d, serving as a retaining device for the charge 200. In this case, each part has a minor axial slot 67 which runs up to the circumferential recess 65, such that the venting device is constituted of the major gaps 66 between the parts of the positioning device 64 and the minor axial slots 67 present in the parts. The axial slot 67 improves flexion of the parts as well as venting. For venting, gas can travel through the axial slot 67 and then along the circumferential recess 65 to reach the environment.

Figure 3A:
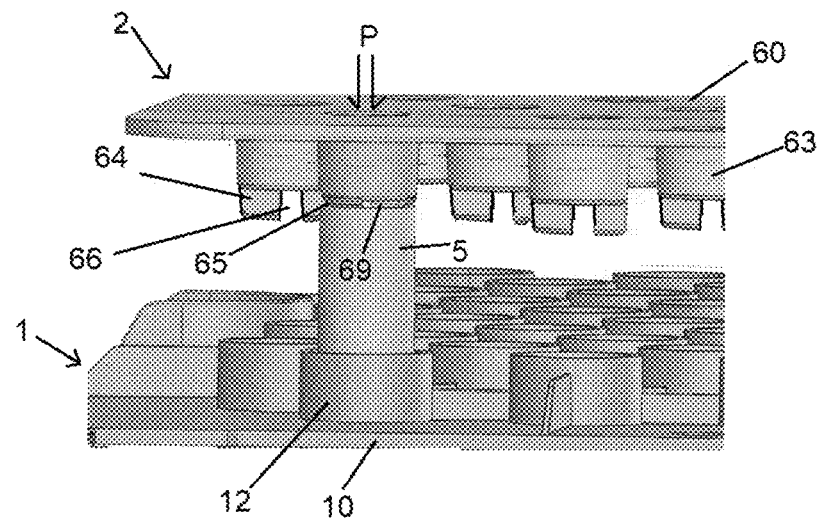
FIG. 3A shows a charge device in position with a positioning device fitted into a receptacle in perspective from above.

FIG. 3A shows a charge device 2 in position with a positioning device 64 fitted into a receptacle 5 in perspective view from above and to the side. The receptacle 5 is located in a receptacle barrel 12, the receptacle barrel 12 being held in position, along with other receptacle barrels of the receptacle device 1, by a receptacle support 10. In this case, the receptacle 5 is resting on a base at the bottom of the receptacle barrel 12 (not shown). The charge barrel 63 is held in position, along with other charge barrels of the charge device 2, by a charge support 60. The positioning device 64 has been inserted into the receptacle 5. The entire positioning device 64 apart from a small portion at its top end are located in the receptacle 5. The top of the positioning device 64 is prevented from entering into the receptacle barrel 12 because its radius at the top is greater than the inner radius of the receptacle 5. An accessible channel 69 constituted by the top part of the major gap in the positioning device 66 which is maintained above the top of the receptacle, allowing venting of gas from inside the positioning device 64, either directly or via a circumferential recess in the positioning device 65. An arrow P shows the action a pressurized gas to act as an ejection device to eject a charge 200 (not shown) from the charge barrel 63, through the positioning device 64, into the receptacle 5.

Figure 3B:
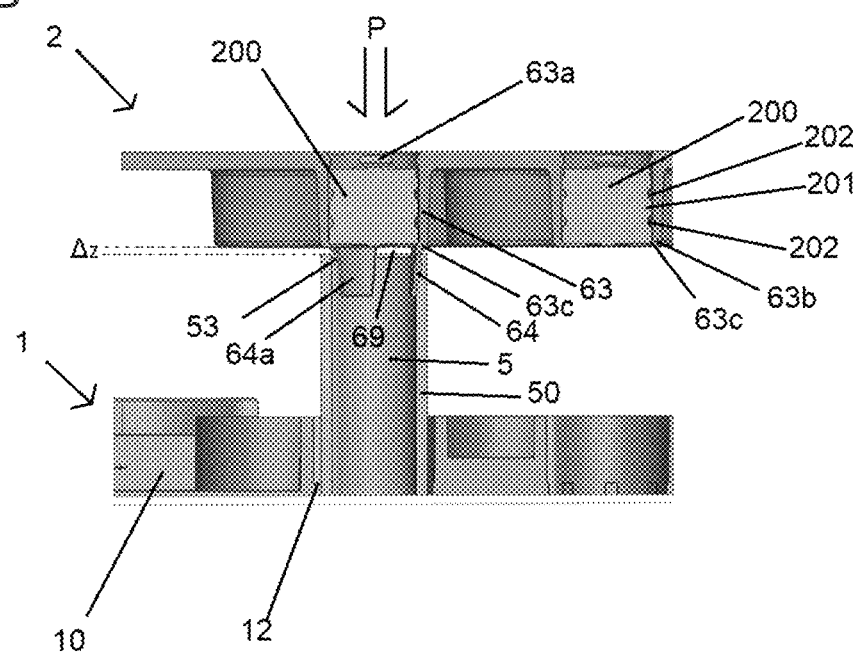
FIG. 3B shows a charge device in position with a positioning device fitted into a receptacle in cross-section from the side.

FIG. 3B shows a charge device 2 in position with a positioning device 64 fitted into a receptacle 5 in cross-section from the side. The charge barrels 63 are held in position by a charge support 60. In this case, the charge barrel 63 and the positioning device 64 are constituted as an integral member. The receptacle 5 is located in a receptacle barrel 12. The receptacle barrels 12 of the receptacle device 1 are held in position by a receptacle support 10. The positioning device 64 is located inside the receptacle 5 with its outer wall 64A in contact with the inner wall of the receptacle wall 50. The positioning device 64 has entered the receptacle 5 via a superior entry aperture 53. The top end of the positioning device 64 remains outside the receptacle 5 with a clearance of Az providing an accessible channel 69 for venting air from inside the positioning device 64. The charge 200 inside the charge barrel 63 is held in position from above by a protrusion 63A on the inner wall of the charge barrel 63, the protrusion 63A serving as a retaining device for the charge 200 by resisting upward movement of the charge 200, and from below by an inward taper 63C towards the bottom rim 63B of the charge barrel 63, constituting a constriction and serving as a retaining device for the charge 200 by resisting downward movement of the charge 200. The charge has circumferential protrusions 201 and recesses 202 in its radius to help keep it in position, thus acting as a retaining device of the protrusion and recess type incorporated into the charge 200. A pressurized gas P can be applied to the top of the charge 200 to push it downwards, thus expelling it from the charge barrel 63, via the positioning device 64, into the receptacle 5.

Figure 4A:
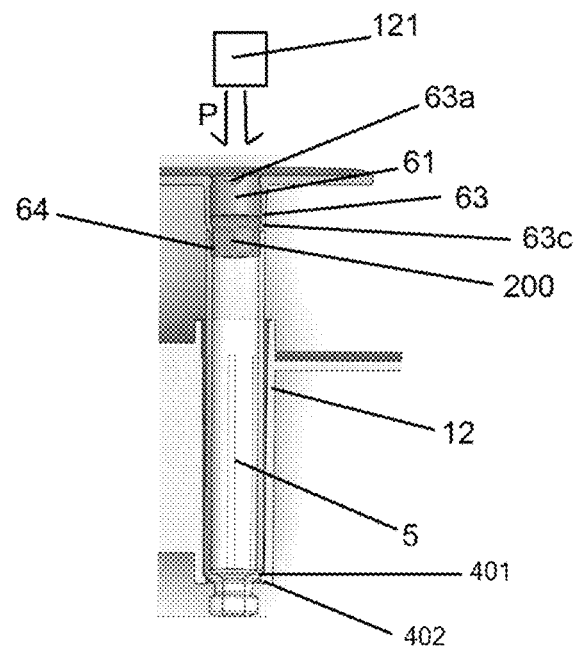
FIG. 4A shows a cross-section view from the side of a charge device in position during ejection of a charge.

FIG. 4A shows a cross-section view from the side of a charge barrel 63 in position during ejection of a charge 200. The arrow P indicates pressurized gas from an ejection device 121 for urging the charge 200 downwards, out of the charge barrel 63, through the positioning device 64, into the receptacle 5, which is located in a receptacle barrel 12. A shoulder 401 towards the bottom of the receptacle 5 and an inward protrusion 402 of the receptacle barrel 12 serve as cooperating parts to position the receptacle 5, with the receptacle 5 resting on the receptacle barrel 12 by abutment of the shoulder 401 with the protrusion 402. The charge is held in the interior 61 of the charge barrel 63 from above by a protrusion 63A in the charge barrel 63, which serves as a retaining device for the charge 200 by resisting upward movement of the charge 200. The ejection device 121 applies sufficient force to push the charge 200 past the narrowing at the lower end 63C of the charge barrel 63, which constitutes a constriction and serves as a retaining device for the charge 200, by radial compression of the charge 200. In the figure, the charge 200 has been pushed mostly out of the charge barrel and its bottom end has reached the bottom tip of the positioning device 64. The positioning device 64 has a smaller inner radius than the charge barrel 63 and the charge 200 and the charge 200 is compressed radially by the inner walls of the positioning device 64. Once the charge 200 leaves the positioning device 64, it will expand to make sealing contact with the inner walls of the receptacle.

Figure 4B:
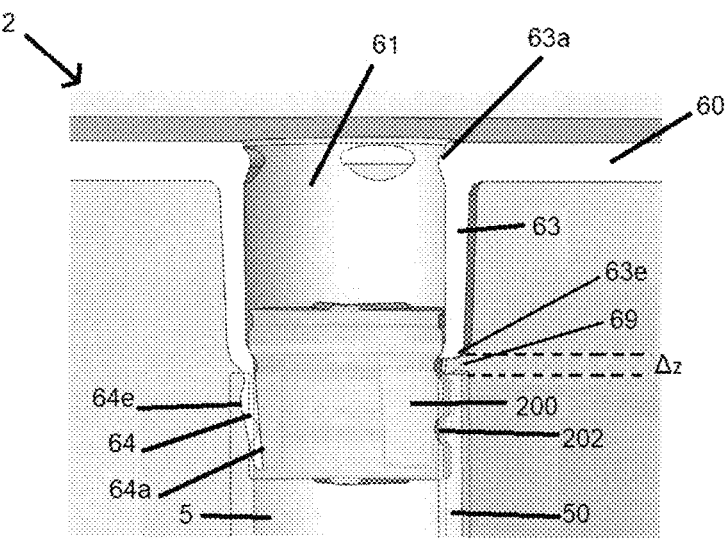
FIG. 4B shows a zoomed in cross-section view from the side of a charge device in position during ejection of a charge.

FIG. 4B shows a zoomed in cross-section view from the side of a charge device 2 in position during ejection of a charge 200 from the interior 61 of the charge barrel 63 into a receptacle 5. A downward direction is defined by a charge support 60, which is shown as a horizontal lamina. The charge 200 has moved downward from a position in which it held from above by a protrusion 63A in the charge barrel 63, the protrusion 63A serving as a retaining device for the charge 200 by resisting upward movement of the charge 200, and from below by a narrowing of the charge barrel 63C, the narrowing 63C constituting a constriction and serving as a retaining device for the charge by resisting downward movement of the charge 200. The charge 200 has moved partially past the narrowing 63C of the charge barrel 63, passing rest points in which the inward recesses 202 of the charge 200 correspond with the narrowing 63C at the lower end of the charge barrel 63. It can be seen that the positioning device 64 has been flexed inwards by pivoting around a contact between its thickest point 64e and the inner surface of the receptacle wall 50. This causes the inner surface 64A of the positioning device 64 to reduce from top to bottom. An accessible channel 69 is shown at the top of the receptacle 5, where the positioning device clears the top of the receptacle 5 by a difference Δz. Air pushed by the charge 200 as it travels downwards can escape via the accessible channel 69.

EXAMPLES

The following examples serve to further explain this disclosure. They are exemplary and do not limit the scope of the invention.

Example 1

A nest of 100 stoppers (charges) was provided according to FIG. 2A. The stoppers were made of silicon-based polymer having a Shore-A hardness of 30. The charge barrels and the charge support were made of polypropylene having a Shore-D hardness of 70. The stoppers were of polyisobutylene. The charge barrels had positioning device according to FIG. 2B. The positioning device were made of silicon-based polymer having a Shore-A hardness of 35. A nest accommodating 100 pre-crimped syringe barrels was provided, the pattern of the syringe barrels complementing that of the charge barrels. The syringe barrels were filled with water, a 1.1 cm air gap was left at the top of each. The nest of stoppers was positioned in correspondence with the nest of syringe barrels by introducing the positioning device in to the top aperture of the syringe barrels. The stoppers were ejected from the charge barrels into the syringe barrels by pressing from above with motorized rods. The stoppers were introduced into the receptacles, whilst the positioning device were simultaneously removed from the syringe barrels. The syringe barrels were thus closed. The example was repeated 100 times at atmospheric pressure.

Example 2

Example 1 was repeated with the material for the charge device (charge barrels, charge support and positioning device) replaced with polypropylene having a Shore-D hardness of 70 and with the material for the stoppers replaced with bromobutyl rubber having a Shore-A hardness of 70.

Examples 3 & 4

Examples 1 and 2 were repeated, except that the major gaps 66 were absent from the positioning device 64.

Examples 5 to 8

Examples 1 to 4 were repeated, except in a vacuum chamber at a pressure of 100 Pa.

Examples 9 to 16

Examples 1 to 8 were repeated, except with no positioning device.

Examples 17 to 24

Examples 1 to 8 were repeated, except with a positioning device according to FIG. 2D.

Results

Results were obtained as provided in the below table considering the following meaning for the performance parameters: =unfavorable, −−=very unfavorable, +=favorable, ++=very favorable, +++=most favorable, NA=not applicable.

| Example | Stoppering success rate | Purity of receptacle contents | Ease of fitting the device parts | Force required to insert positioning device |
| --- | --- | --- | --- | --- |
| 1 | +++ | ++ | ++ | ++ |
| 2 | +++ | + | +++ | ++ |
| 3 | − | − | ++ | − |
| 4 | − | − | +++ | − |
| 5 | +++ | ++ | ++ | ++ |
| 6 | +++ | + | +++ | ++ |
| 7 | +++ | ++ | ++ | ++ |
| 8 | +++ | + | +++ | ++ |
| 9 | −−− | ++ | − | NA |
| 10 | −−− | ++ | − | NA |
| 11 | −−− | ++ | − | NA |
| 12 | −−− | ++ | − | NA |
| 13 | − | ++ | − | NA |
| 14 | + | ++ | − | NA |
| 15 | − | ++ | − | NA |
| 16 | + | ++ | − | NA |
| 17 | +++ | ++ | ++ | +++ |
| 18 | +++ | + | +++ | +++ |
| 19 | − | − | ++ | − |
| 20 | − | − | +++ | − |
| 21 | +++ | ++ | ++ | +++ |
| 22 | +++ | + | +++ | +++ |
| 23 | +++ | ++ | ++ | +++ |
| 24 | +++ | + | +++ | +++ |

As can be seen from the results, the positioning device allowed stoppering to be carried out at atmospheric pressure. Without the positioning device, pressure built up in the syringe barrel causing spilling and damage to the syringe barrels. The positioning device also allowed a softer material for the charge nest to be employed. This increased the purity of the product because it avoided the creation of dust through mechanical wear. The provision of venting slots in the positioning device improved the success rate of the stoppering by avoiding a build-up of pressure. Additional slots in the sectional parts of the positioning device (according to FIG. 2D) improved the ease of insertion and reduced the force required.

REFERENCE LIST

P1 Provision step
P2 Filling step
P3 Positioning step
P4 Closure step
1 Receptacle device
2 Charge device
5 Receptacle
10 Receptacle support
12 Receptacle barrel
50 Receptacle wall
53 Entry aperture of receptacle
60 Charge support
61 Interior of charge barrel
62 Rounded corner of charge support
63 Charge barrel
63A Protrusion of charge barrel (retaining device)
63B Bottom rim of charge barrel
63C Inner taper of side wall (retaining device)

64 Positioning device
64A Inner surface of positioning device
64B Outer surface of positioning device
64c Lower end of positioning device
64d Bevel at tip of positioning device
64e Apex below circumferential recess
64f Upper end of positioning device
65 Circumferential recess in positioning device (venting device and flexion device)
66 Major gap in positioning device (venting device)
67 Minor axial slot in positioning device (venting device)
69 Accessible channel (venting device)
121 Ejection device
200 Charge
201 Circumferential protrusion of the charge
202 Circumferential recess of the charge
300 Exit aperture
401 Shoulder of receptacle
402 Inward protrusion of receptacle barrel
P Pressurized gas
$\Delta z$ clearance of top of positioning device above top of receptacle

The invention claimed is:

1. A charge device comprising:
    a charge barrel having an exit aperture and a flexible positioning device at the exit aperture, wherein the flexible positioning device comprises an outer face with a top end, the flexible positioning device having a circumferential recess positioned in the outer face where the top end meets the charge barrel, and wherein, below the circumferential recess, the flexible positioning device has a thickest point after which the flexible positioning device tapers towards a lower end; and
    a charge located inside the charge barrel, wherein the charge barrel is adapted and arranged so that the charge is able to exit the charge barrel via the exit aperture.

2. The charge device of claim 1, further comprising a plurality of the charge barrels.

3. The charge device of claim 1, wherein the charge barrel further comprises a venting device adapted and arranged to allow gas to escape from the charge barrel as the charge exits the charge barrel through the exit aperture.

4. The charge device of claim 3, wherein the venting device is a hole or a slot.

5. The charge device of claim 1, wherein the charge barrel comprises a polymer.

6. The charge device of claim 1, wherein the charge barrel has a length that is not more than 3 times a length of the charge.

7. The charge device of claim 1, wherein the charge barrel is configured so that a distance of the charge from the exit aperture is not more than 4 times a length of the charge.

8. The charge device of claim 1, wherein the flexible positioning device is an incomplete hollow prism or cylinder having one or more holes in a sidewall.

9. The charge device of claim 1, wherein the flexible positioning device has an inner diameter that is smaller than an inner diameter of the charge barrel.

10. The charge device of claim 1, further comprising a sterile container, wherein the charge barrel is located inside the sterile container.

11. The charge device of claim 1, wherein the charge is selected from a group consisting of a plunger, a stopper, a seal, and a seal cap.

12. The charge device of claim 1, wherein the charge comprises a material having a Young's modulus less than that of the charge barrel.

13. The charge device of claim 1, wherein the charge comprises a thermoplastic elastomer.

14. The charge device of claim 1, wherein the circumferential recess is configured to facilitate air flow and flexion of the positioning device.

15. A kit comprising:
    a charge device comprising a charge barrel and a charge, the charge barrel having an exit aperture and a flexible positioning device at the exit aperture, the charge being located inside the charge barrel, wherein the charge barrel is adapted and arranged so that the charge is able to exit the charge barrel via the exit aperture, and wherein the flexible positioning device comprises an outer face with a top end, the flexible positioning device having a circumferential recess positioned in the outer face where the top end meets the charge barrel, and wherein, below the circumferential recess, the flexible positioning device has a thickest point after which the flexible positioning device tapers towards a lower end; and
    a receptacle device comprising a receptacle barrel having a receptacle located inside it, wherein the receptacle has an entry aperture that is configured to receive the charge from the charge barrel through the entry aperture.

16. The kit of claim 15, wherein one the receptacle is selected from a group consisting of a cartridge, a syringe, a syringe precursor, and a vial.

17. The kit of claim 15, wherein the charge barrel further comprises a venting device adapted and arranged to allow gas to escape from the charge barrel as the charge exits the charge barrel through the exit aperture.

18. The kit of claim 15, wherein the flexible positioning device has an exterior diameter, which is smaller than an interior diameter of the receptacle so that the flexible positioning device can be inserted into the receptacle.

19. The kit of claim 15, wherein, when the charge is received in the receptacle through the entry aperture, the flexible positioning device has a top end having a vent channel that remains outside of the entry aperture of the receptacle.

20. A charge device comprising:
    a charge barrel having an exit aperture and a flexible positioning device at the exit aperture, wherein the flexible positioning device comprises an outer face with a top end, the flexible positioning device having a circumferential recess positioned in the outer face where the top end meets the charge barrel;
    a charge located inside the charge barrel, wherein the charge barrel is adapted and arranged so that the charge is able to exit the charge barrel via the exit aperture; and
    a venting device adapted and arranged to allow gas to escape from the charge barrel as the charge exits the charge barrel through the exit aperture, wherein the venting device is in the flexible positioning device and extends from a bottom end towards the top end and through the circumferential recess.

* * * * *